US00PP21512P2

(12) United States Plant Patent
Head et al.

(10) Patent No.: US PP21,512 P2
(45) Date of Patent: Nov. 23, 2010

(54) ***AZALEA* PLANT NAMED 'RLH1-3P3'**

(50) Latin Name: *Rhododendron hybrida*
Varietal Denomination: RLH1-3P3

(75) Inventors: Robert Harold Head, Seneca, SC (US); Lisa Jones Head, Seneca, SC (US)

(73) Assignee: Head's Select, Inc., Seneca, SC (US)

( * ) Notice: Subject to any disclaimer, the term of this patent is extended or adjusted under 35 U.S.C. 154(b) by 0 days.

(21) Appl. No.: 12/586,297

(22) Filed: Sep. 18, 2009

(51) Int. Cl.
*A01H 5/00* (2006.01)

(52) U.S. Cl. ..... Plt./238
(58) Field of Classification Search ..... Plt./238
See application file for complete search history.

*Primary Examiner*—Annette H Para
(74) *Attorney, Agent, or Firm*—C. A. Whealy

(57) ABSTRACT

A new and distinct cultivar of *Azalea* plant named 'RLH1-3P3', characterized by its compact, upright, outwardly spreading and globose plant habit; freely branching habit; dense, bushy and vigorous growth habit; small evergreen and persistent dark green-colored leaves that do not abscise during the winter; freely flowering habit during spring and from summer until frost in autumn; large white-colored flowers that are not persistent; single star-shaped flower form; and excellent garden performance.

2 Drawing Sheets

Botanical designation: *Rhododendron hybrida.*
Cultivar denomination: 'RLH1-3P3'.

BACKGROUND OF THE INVENTION

The present Invention relates to a new and distinct cultivar of *Azalea* plant, botanically known as *Rhododendron hybrida,* an evergreen *Azalea*, and hereinafter referred to by the name 'RLH1-3P3'.

The new *Azalea* plant is a product of a planned breeding program conducted by the Inventors in Long Creek, Oconee County, S.C. The objective of the breeding program is to create new compact evergreen *Azalea* plants having dense growth habit, large attractive flowers, good foliage retention during the winter, consistent summer reblooming qualities and cold hardiness.

The new *Azalea* plant originated from a cross-pollination made by the Inventors in 1996, in Long Creek, Oconee County, S.C., of a proprietary selection of *Rhododendron hybrida* identified as code number RLH-1800-WS, not patented, as the female, or seed, parent with *Rhododendron hybrida* 'September Song', not patented, as the male, or pollen, parent. The new *Azalea* plant was discovered and selected by the Inventors as a single flowering plant within the progeny of the stated cross-pollination in a controlled greenhouse environment in Long Creek, Oconee County, S.C. in 2000.

Asexual reproduction of the new *Azalea* plant by semi-hardwood stem cuttings in a controlled greenhouse environment in Long Creek, Oconee County, S.C. since 2005, has shown that the unique features of this new *Azalea* plant are stable and reproduced true to type in successive generations.

SUMMARY OF THE INVENTION

Plants of the new *Azalea* have not been observed under all possible environmental conditions. The phenotype may vary somewhat with variations in environment such as temperature and light intensity without, however, any variance in genotype. The following traits have been repeatedly observed and are determined to be the unique characteristics of 'RLH1-3P3'. These characteristics in combination distinguish 'RLH1-3P3' as a new and distinct *Azalea* cultivar:

1. Compact, upright, outwardly spreading and globose plant habit.
2. Freely branching habit; dense, bushy and vigorous growth habit.
3. Small evergreen and persistent dark green-colored leaves that do not abscise during the winter.
4. Freely flowering habit during spring and from summer until frost in autumn.
5. Large white-colored flowers that are not persistent.
6. Single star-shaped flower form.
7. Excellent garden performance.

Plants of the new *Azalea* differ from plants of the female parent selection in the following characteristics:

1. Plants of the new *Azalea* are more spreading than plants of the female parent selection.
2. Plants of the new *Azalea* have darker green-colored leaves than plants of the female parent selection.
3. Flowers of plants of the new *Azalea* are white in color whereas flowers of plants of the female parent selection are salmon pink in color.

Plants of the new *Azalea* differ from plants of the male parent, 'September Song', in the following characteristics:

1. Plants of the new *Azalea* are more spreading and more freely branching than plants of 'September Song'.
2. Plants of the new *Azalea* have smaller and darker green-colored leaves than plants of 'September Song'.
3. Flowers of plants of the new *Azalea* are white in color whereas flowers of plants of 'September Song' are red in color.

Plants of the new *Azalea* can be compared to the plants of 'Robleg', disclosed in U.S. Plant Pat. No. 15,227. In side-by-side comparisons conducted in Long Creek, Oconee County, S.C., plants of the new *Azalea* differed from plants of 'Robleg' in the following characteristics:

1. Plants of the new *Azalea* were more freely branching than plants of 'Robleg'.
2. Plants of the new *Azalea* were more freely flowering than plants of 'Robleg'.

3. Flowers of plants of the new *Azalea* were undulate and ruffled whereas flowers of plants of 'Robleg' were flat.
4. Plants of the new *Azalea* flowered during the spring, summer and autumn whereas plants of 'Robleg' flowered only in the spring and autumn.

BRIEF DESCRIPTION OF THE PHOTOGRAPHS

The accompanying colored photographs illustrate the overall appearance of the new *Azalea* plant. These photographs show the colors as true as it is reasonably possible to obtain in colored reproductions of this type. Colors in the photographs may differ slightly from the color values cited in the detailed botanical description, which accurately describe the colors of the new *Azalea* plant.

The photograph on the first sheet comprises a side perspective view of a typical flowering plant of 'RLH1-3P3' grown in a container.

The photograph on the second sheet is a close-up view of a typical flower of 'RLH1-3P3'.

DETAILED BOTANICAL DESCRIPTION

The aforementioned photographs and following observations and measurements describe plants grown in Long Creek, Oconee County, S.C. in 5.7-liter containers, in a polypropylene-covered shade house during the late summer and under commercial production conditions. During the production of the plants, day temperatures ranged from −5° C. to 40° C. and night temperatures ranged from −25° C. to 35° C. Plants used for the photographs were five years old and plants used for the description were two years old. In the following description, color references are made to The Royal Horticultural Society Colour Chart, 2007 Edition, except where general terms of ordinary dictionary significance are used.

Botanical classification: *Rhododendron hybrida* 'RLH1-3P3'.

Commercial classification: Evergreen-type *Azalea*.

Parentage:

*Female, or seed, parent.*—Proprietary selection of *Rhododendron hybrida* identified as code number RLH-1800-WS, not patented.

*Male, or pollen, parent.*—*Rhododendron hybrida* 'September Song', not patented.

Propagation:

*Type.*—By semi-hardwood stem cuttings.

*Time to initiate roots, summer.*—About 25 to 30 days at temperatures of 27° C. to 30° C.

*Time to initiate roots, winter.*—About 35 to 45 days at temperatures of 16° C. to 17° C.

*Time to produce a rooted young plant, summer.*—About 60 to 70 days at temperatures of 27° C. to 30° C.

*Time to produce a rooted young plant, winter.*—About 80 to 100 days at temperatures of 16° C. to 17° C.

*Root description.*—Fine, fibrous; initially white, close to 155C, in color becoming closer to 159C and eventually 164A with development.

*Rooting habit.*—Freely branching; dense.

Plant description:

*Plant form and growth habit.*—Perennial and evergreen flowering shrub; compact, upright, outwardly spreading and globose plant habit; freely branching habit; dense, bushy and vigorous growth habit; moderate growth rate; freely flowering habit with numerous showy single flowers.

*Branching habit.*—Freely branching habit with about eight to ten basal branches developing on one year old plants; pinching (removal of terminal apex) will enhance lateral branch development.

*Plant height, soil level to top of flowers.*—About 25 cm to 35 cm.

*Plant diameter, area of spread.*—About 25 cm to 30 cm.

*Lateral branch description.*—Length: About 2 cm to 15 cm. Diameter at base: About 2 mm to 4 mm. Internode length: About 3 mm to 10 mm. Strength: Strong. Aspect: Upright and outwardly positioned. Texture, developing: Pubescent, fine greyed orange-colored hairs. Texture, mature: Woody; pubescent, fine greyed orange-colored hairs. Color, developing: Close to N144D. Color, semi-hardwood: Close to 144A becoming close to N199D with development. Color, mature: Close to N199C.

*Foliage description.*—Arrangement: Alternate; simple. Foliage retention: Very good winter foliage retention has been observed on plants of the new *Azalea*. *Length: About* 1 cm to 3.2 cm. Width: About 4 mm to 15 mm. Shape: Obelliptic. Apex: Rounded to obtuse; mucronulate. Base: Cuneate to attenuate; equilateral. Margin: Entire; slightly revolute; ciliate. Venation pattern: Pinnate; reticulate. Texture, upper and lower surfaces: Pubescent; coriaceous, tough. Color: Developing leaves, upper surface: Close to 141A to 141B. Developing leaves, lower surface: Close to 143A. Fully expanded leaves, upper surface: Close to 139A; venation, close to 144A. Fully expanded leaves, lower surface: Close to 138A; venation, close to 144C. Petiole: Length: About 3 mm to 5.5 mm. Diameter: About 0.8 mm to 1.3 mm. Texture, upper and lower surfaces: Pubescent. Color: Developing leaves, upper surface: Close to 143C. Developing leaves, lower surface: Close to 144C. Fully expanded leaves, upper surface: Close to 144A. Fully expanded leaves, lower surface: Close to 143C.

Flower description:

*Natural flowering season.*—Spring, April to May, and then re-flowering during the summer and autumn, July to October, until frost in South Carolina.

*Flower arrangement and appearance.*—Single star-shaped flowers arranged in clusters at terminals and sub-terminals with usually about one to three flower buds and two to three flowers per cluster; uniform and freely flowering habit; flowers face upward or outward.

*Flower appearance.*—Flowers rotate and rose-like; single flower form; flowers with a single whorl of five petals.

*Flower longevity.*—Durable and long-lasting; flowers last about five to ten days on the plant and about three to five days as a cut flower; flowers not persistent.

*Fragrance.*—None detected.

*Flower diameter.*—About 6 cm to 7.5 cm.

*Flower depth.*—About 3 cm to 3.5 cm.

*Flower bud* (*before showing color*): Length: About 1.2 cm to 1.5 cm. Diameter: About 5 mm to 6.5 mm. Shape: Ovoid. Color: Close to 143A.

*Petals.*—Arrangement: Single star-shaped flowers have a single whorl of five petals, fused at the base forming a wide funnel-shaped corolla. Length: About 2 cm to 2.5 cm. Width: About 2 cm to 2.8 cm. Shape: Broadly rotund to orbicular. Apex: Retuse to obtuse; revolute to involute; undulate and ruffled. Margin: Entire; undulate and ruffled. Texture, upper and lower surfaces: Smooth, glabrous; rugulose; waxy to velvety in appearance. Color: When opening, upper surface: Close to NN155C; spots and speckles, close to N144C. When opening, lower surface: Close to NN155C. Fully opened, upper surface: Close to NN155D; spots and speckles, close to N144C. Fully opened, lower surface: Close to NN155D.

*Sepals.*—Arrangement: Five in a single whorl, fused at the base forming a campanulate to star-shaped corona. Length: About 2.8 mm to 4 mm. Width: About 2.5 mm to 3 mm. Shape: Ovate to rotund. Apex: Ovate to rotund; erosulate and ciliate. Base: Truncate. Margin: Erosulate; ciliate. Texture, upper surface: Glabrous. Texture, lower surface: Lightly covered with sericeous pubescence. Color, upper and lower surfaces: Close to 143C; towards the base, close to N144D.

*Peduncles.*—Length: About 1 mm to 1.5 mm. Diameter: About 2 mm to 3 mm. Angle: Mostly upright. Strength: Strong. Texture: Pubescent. Color: Close to 144B; at maturity, close to N199D.

*Pedicels.*—Length: About 7.5 mm to 9.5 mm. Diameter: About 2 mm to 2.5 mm. Angle: Upright to outwardly. Strength: Strong. Texture: Pubescent. Color: Close to 144B.

*Reproductive organs.*—Androecium: Quantity of stamens per flower: About ten. Filament length: About 2.8 cm to 3.2 cm. Filament color: Close to NN155C. Anther shape: Porandrous with four oblong, tubular to lunate-shaped pollen sacks basifixed to the filament. Anther length: About 2.5 mm to 3 mm. Anther color: Close to 165C. Pollen amount: Moderate. Pollen color: Close to NN155B. Gynoecium: Pistil length: About 4.5 cm to 4.8 cm. Stigma shape: Round to flattened (capitate). Stigma color: Close to 143C. Style length: About 4.4 cm to 4.7 cm. Style color: Close to NN155C. Ovary color: Close to 141B.

*Fruits.*—Quantity per plant: About three to five. Length: About 5 mm to 7.5 mm. Diameter: About 3.5 mm to 4.5 mm. Texture: Slightly rugulose to scabridulose; glandular, setaceous. Color: Close to 143A; at maturity, close to 137C and becoming closer to 200C with development.

*Seeds.*—Quantity per fruit: About 200 to 300. Length: About 0.6 mm to 0.9 mm. Diameter: About 0.2 mm to 0.3 mm. Color: Close to 164B.

Weather/temperature tolerance: Plants of the new *Azalea* have been observed to be very tolerant to rain and wind. Plants of the new *Azalea* have been observed to tolerate temperatures from about −25° C. to about 40° C. and are suitable for USDA Hardiness Zones 6B to 9.

Disease/pest resistance: Plants have not been observed to be resistant to pathogens and pests common to *Azaleas*.

It is claimed:

1. A new and distinct cultivar of *Azalea* plant named 'RLH1-3P3' as illustrated and described.

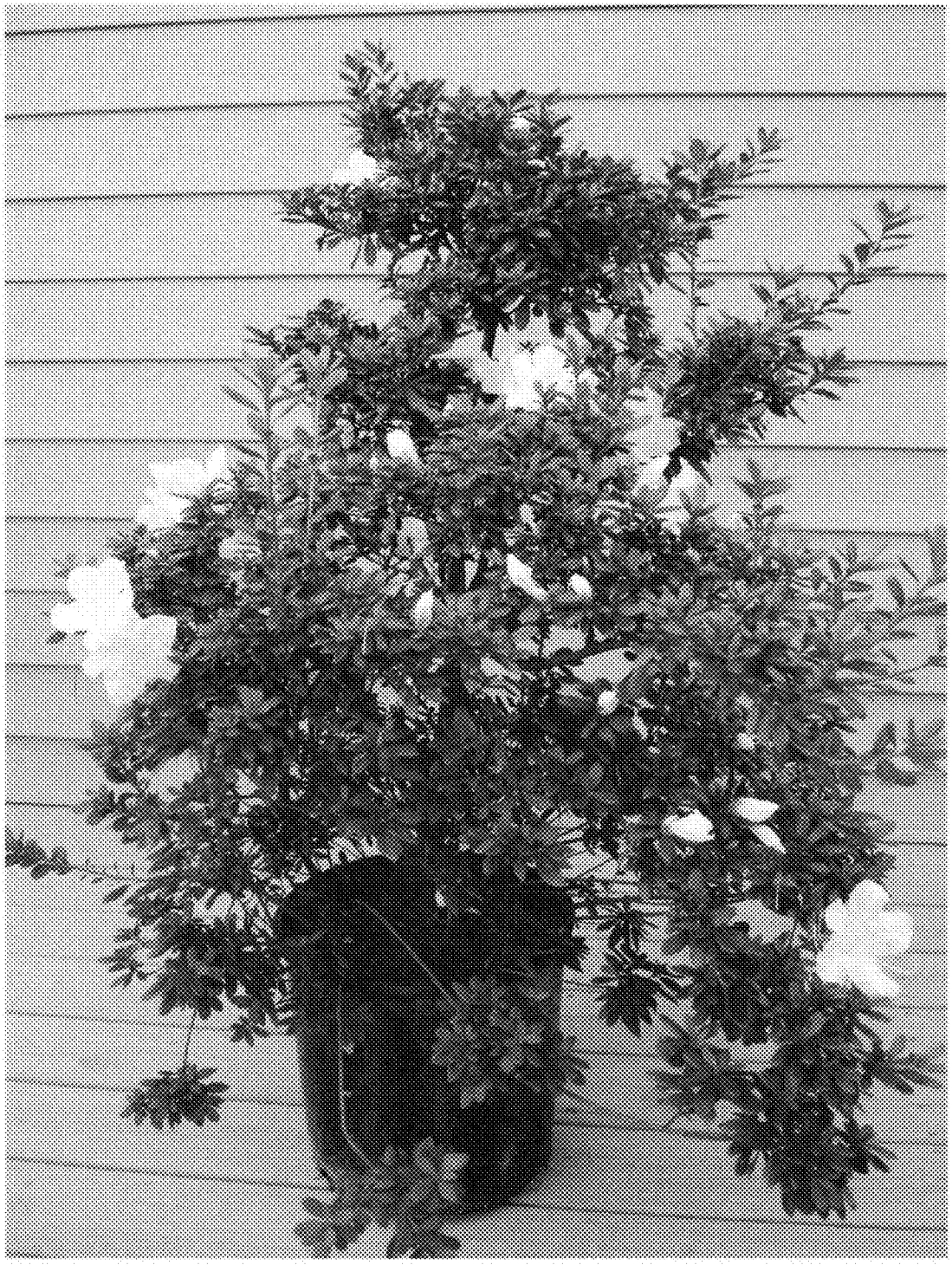

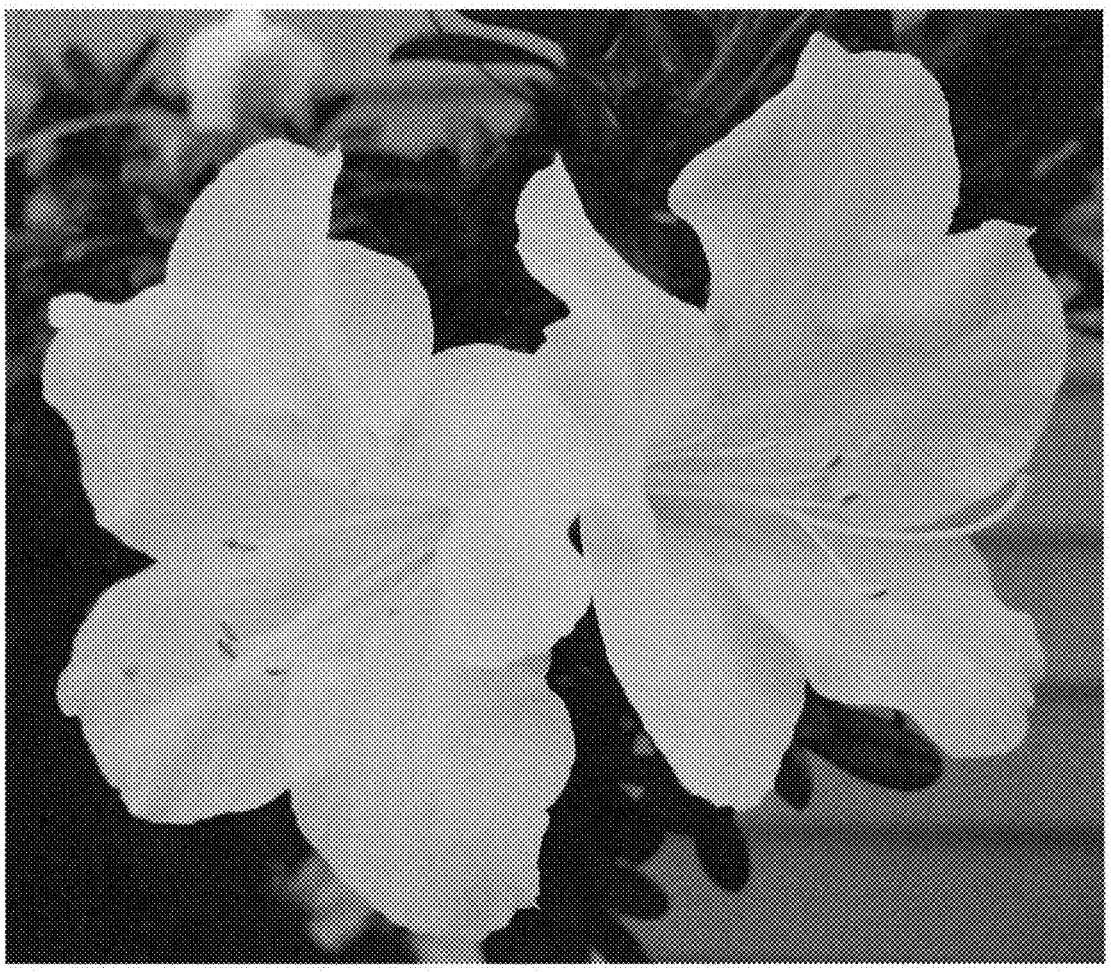

* * * * *